United States Patent
Guo et al.

(10) Patent No.: US 7,175,750 B2
(45) Date of Patent: Feb. 13, 2007

(54) SYSTEM AND METHOD FOR TEMPERATURE GRADIENT CAPILLARY ELECTROPHORESIS

(75) Inventors: Zhiyong Guo, State College, PA (US); Zhaowei Liu, Port Matilda, PA (US); Qingbo Li, State College, PA (US)

(73) Assignee: SpectruMedix LLC, State College, PA (US)

( * ) Notice: Subject to any disclaimer, the term of this patent is extended or adjusted under 35 U.S.C. 154(b) by 407 days.

(21) Appl. No.: 10/287,826

(22) Filed: Nov. 5, 2002
(Under 37 CFR 1.47)

(65) Prior Publication Data

US 2003/0138821 A1    Jul. 24, 2003

Related U.S. Application Data

(63) Continuation of application No. PCT/US01/27440, filed on Sep. 4, 2001.

(60) Provisional application No. 60/229,302, filed on Sep. 1, 2000.

(51) Int. Cl.
*G01N 27/447* (2006.01)

(52) U.S. Cl. ...................... 205/451; 204/456

(58) Field of Classification Search ........ 204/451–458, 204/461, 466–467
See application file for complete search history.

(56) References Cited

U.S. PATENT DOCUMENTS

| | | | |
|---|---|---|---|
| 5,066,377 A | 11/1991 | Rosenbaum et al. | |
| 5,068,176 A | 11/1991 | Vijg et al. | |
| 5,734,058 A * | 3/1998 | Lee ............................. | 546/176 |
| 5,736,025 A | 4/1998 | Smith et al. | |
| 5,795,720 A | 8/1998 | Henco et al. | |
| 5,871,908 A | 2/1999 | Henco et al. | |
| 5,935,522 A | 8/1999 | Swerdlow et al. ............ | 422/70 |
| 5,998,147 A | 12/1999 | Petit et al. | |
| 6,017,704 A | 1/2000 | Herman et al. ................ | 435/6 |
| 6,036,831 A | 3/2000 | Bishop | |

(Continued)

FOREIGN PATENT DOCUMENTS

| | | |
|---|---|---|
| EP | 0 329 341 | 8/1989 |

(Continued)

OTHER PUBLICATIONS

Gao et al. ("High-Throughput Detection of Unknown Mutations by Using Multiplexed Capillary Electrophoresis with Poly(vinylpyrrolidone) Solution," Anal. Chem. 2000, 72, 2499-2506.*

(Continued)

*Primary Examiner*—Alex Noguerola

(57) ABSTRACT

The present invention relates to a method for determining the presence of a mutation in a first sample comprising first nucleotides. The reference sample comprising reference nucleotides. The first sample and a reference sample are subjected to electrophoresis in the presence of at least one intercalating dye. During electrophoresis the temperature of the first sample and the reference sample is changed by an amount sufficient to change an electrophoretic mobility of at least one of the first or reference nucleotides. Fluorescence intensity data are obtained. The fluorescence intensity data are indicative of the presence of the first and reference nucleotides. At least one of the first sample or reference samples comprises products resulting from a polymerase chain reaction (PCR), the products not having been desalted prior to electrophoresis.

17 Claims, 9 Drawing Sheets

U.S. PATENT DOCUMENTS

| | | | |
|---|---|---|---|
| 6,265,171 B1 | 7/2001 | Herman et al. ............... 435/6 |
| 6,265,557 B1 | 7/2001 | Diamond et al. |
| 6,398,933 B1 | 6/2002 | Scott |
| 6,475,721 B2 | 11/2002 | Kleiber et al. |
| 6,486,309 B1 | 11/2002 | Gerber et al. |
| 6,613,508 B1 | 9/2003 | Ness et al. |
| 2002/0012902 A1 | 1/2002 | Fuchs et al. ............... 435/6 |
| 2002/0042060 A1 | 4/2002 | Raees et al. ............... 435/6 |

FOREIGN PATENT DOCUMENTS

| | | |
|---|---|---|
| WO | WO 91/02815 | 3/1991 |
| WO | WO 96/08715 | 3/1996 |
| WO | WO 96/24687 | 8/1996 |
| WO | WO 97/40184 A1 * | 10/1997 |
| WO | WO 01/77386 | 10/2001 |
| WO | WO 02/31199 | 4/2002 |

OTHER PUBLICATIONS

Entries for "Peltier Effect", "thermoelectric heating", "thermoelectric cooling", and "thermoelectric cooler" in the McGraw-Hill Encyclopedia of Science & Technology Online. Downloaded on Jun. 6, 2005.*

Wartell et al. ("Review—Detecting single base substitutions, mismatches and bulges in DNA by temperature gradient gel electrophoresis and related methods," Journal of Chrmoatography A, 806 91998) 169-185.*

Wiese ("Scanning for mutations in the human prion protein open reading frame by temporal temperature gradient gel electrophoresis," Electrophoresis 1995, 16, 1851-1860.*

Jens Schell et al., Detection of point mutations by capillary electrophoresis with temporal temperature gradients, © WILEY-VCH Verlag GmbH, Electrophoresis 1999, 20, pp. 2864-2869.

High-Throughput Detection of Unknown Mutations by Using Multiplexed Capillary Electrophoresis with Polyvinylpyrrolidone Solution, The Ames Laboratory, U.S. Department of Energy by Iowa State University, pp. 1-28.

Paul Taylor et al., Detection of Mutations and Polymorphisms on the WAVE™ DNA Fragment Analysis System, Transgenomic, Inc., Application Note 101, pp. 30-33.

Cecilia Gelfi et al., Detection of point mutations by capillary electrophoresis in liquid polymers in temporal thermal gradients, Electrophoresis 1994, 15, pp. 1506-1511.

K. Khrapko et al., Constant denaturant capillary elecxtrophoresis (CDCE): a high resolution approach to mutational analysis, Nucleic Acids Research, 1994, vol. 22, No. 3, pp. 364-369.

David G. Wang et al., Large-Scale Identification, Mapping, and Genotyping of Single-Nucleotide Polymorphisms in the Human Genome, www.sciencemag.org, SCIENCE, vol. 280, May 15, 1998, pp. 1077-1082.

Mark Chee et al., Accessing Genetic Information with High-Density DNA Arrays, Science Magazine, vol. 274, No. 5287, Issue of Oct. 25, 1996, pp. 610-614.

David Sidransky, Nucleic Acid-Based Methods for the Detection of Cancer, SCIENCE, vol. 278, Nov. 7, 1997, www.sciencemag.org, pp. 1054-1058.

Joseph Alper, Weighing DNA for Fast Genetic Diagnosis, Science Magazine, Vo. 279, No. 5359, Issue of Mar. 27, 2998, pp. 2044-2045.

Detlev Riesner et al., Temperature-gradient gel electrophoresis of nucleic acids: Analysis of conformational transitions, sequence variations, and protein-nucleic acid interactions, Electrophoresis, 1989, 10, pp. 377-389.

Song-hua Ke et al., Selecting DNA fragments for mutation detection by temperature gradient gel electrophoresis: Application to the p53 gene cDNA, Electrophoresis, 1993, 14, pp. 561-565.

Richard M. Myers et al., Detection of single base substitutions in total genomic DNA, Nature, vol. 313, Feb. 7, 1985, pp. 495-498.

Detlev Riesner et al., Temperature-gradient gel electrophoresis for the detection of polymorphic DNA and for quantitative polymerase chain reaction, Electrophoresis, 1992, 13, pp. 632-636.

Ezra S. Abrams et al., Comprehensive Detection of Single Base Changes in Human Genomic DNA Using Denaturing Gradient Gel Electrophoresis and a GC Clamp, Genomics 7, 1990, pp. 463-475.

K. Henco et al., Quantitative PCR: the determination of template copy numbers by temperature gradient gel electrophoresis (TGGE), Nucleic Acids Research, vol. 18, No. 22, 1990, pp. 6733-6734.

Qiufeng Gao et al., 25. High-Speed High- Throughout Mutation Detection, http://www.ornl.gov/sci/techresources/Human_Genome/publicat/00santa/25.html, Research Abstracts, 2000, DOE Human Genome Program.

QIAquick PCR Purification Kit QIAGEN, [retrieved on Aug. 10, 2005]. Retrieved from the Internet: <URL: http://www1.qiagen.com/Products/DnaCleanup/GelPcrSiCleanupSystems/QIAquickPCRPurificationKit.aspx?ShowInfo=1>.

Igloi, Gabor L., "Automated Detection of Point Mutations by Electrophoresis in Peptide-Nucleic Acid-Containing Gels", Bio Techniques, 27:798-808 (1999).

Ray et al., "Peptide nucleic acid (PNA): its medical and biotechnical applications and promise for the future", Department of Physical Chemistry, Chalmers University of Technology, S 412 96, Gothenburg, Sweden, pp. 1041-1060.

* cited by examiner

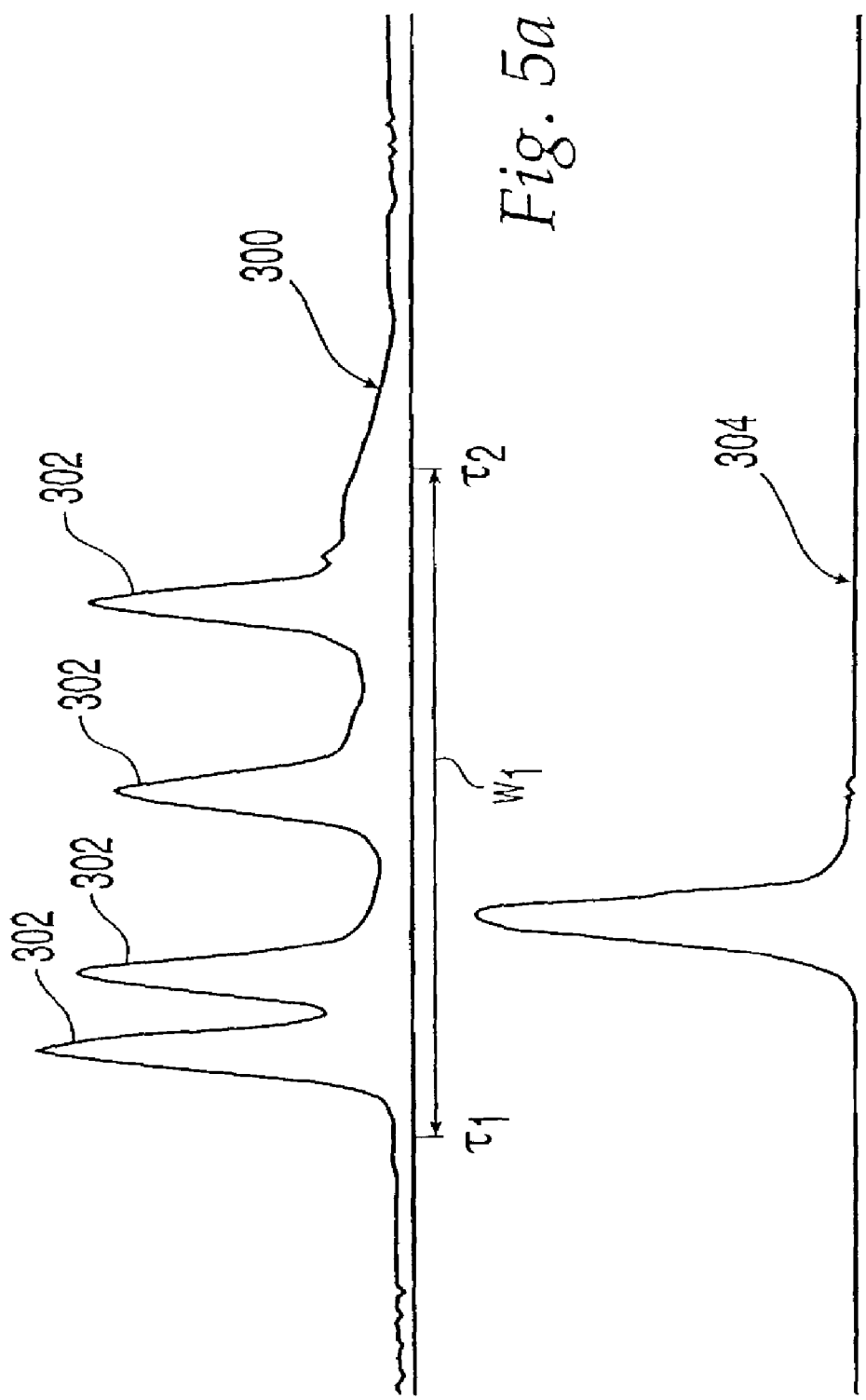

SYSTEM AND METHOD FOR TEMPERATURE GRADIENT CAPILLARY ELECTROPHORESIS

This application claims priority under 35 U.S.C. 120 from PCT/US01/27440, filed on Sep. 04, 2001 and provisional application 60/229,302, filed on Sep. 01, 2000.

FIELD OF THE INVENTION

The invention relates to a system and method for separating materials having temperature-dependent electrokinetic mobilities. More particularly, the invention relates to time-dependent temperature gradient electrokinetic separation of materials including DNA fragments.

BACKGROUND

Detection of mutations and variations occurring in DNA has become increasingly important in the fields of genetics, molecular diagnostics and cancer research. One type of variation, single-nucleotide polymorphism (SNP), has attracted much attention because it is the most common form of genetic variation. This type of single-base substitution in the genome occurs at a frequency of >1% in the human population. A recent estimate is that there is about one SNP per 1000 bp in human DNA. Other types of mutations involve insertion and deletion, and are found to occur at about one per 12 kb. The determination of SNPs can be used to study genetic linkages and for the diagnosis of diseases, especially cancer.

One way to fully characterize a mutation is to perform DNA sequencing on the sample. However, current DNA sequencing techniques are laborious and expensive. Large-scale DNA sequencing to detect mutations is also not efficient because a large portion of the sequences will give negative results considering that mutation is the exception. To save time and cost, rapid screening methods need to be developed to identify both known point mutations and unknown point mutations before any further characterization is undertaken.

The detection of mutation can be accomplished by using oligonucleotide arrays or DNA chips. Even though the number of analysis sites that can be packed into a small area array is very large, one must use multiple spots to span each mismatch (mutation). Using arrays, the match/mismatch discrimination is not entirely definitive, since different sequences have different melting temperatures. Ideally, one would have slightly different temperatures at each site within the array of sites. The other issue is time. In a representative mode of operation, the DNA is applied to the array and hybridization is carried out at 44° C. for 15 h at 40 rpm. The array of sites is then washed and stained before imaging. A third issue is that the DNA arrays are presently quite costly if one wants to span all possible mutations and probe scores of clinical samples at a time. Clearly, further development is needed to speed up the process and to make it more cost effective.

Mutations in DNA are readily detected by mass changes, such as by mass spectroscopic techniques. Substitutions are not so obvious because of the limited mass resolution of instruments that are reasonably accessible at present. Positional switches will not be detected at all because these do not result in a mass change.

A popular electrophoresis method to detect polymorphism is to rely on slight changes in conformations in single-stranded DNA (SSCP). This technique relies on subtle electrophoretic mobility differences between single strands of DNA that have different sequences. The mobility differences arise because, under the proper conditions, the different strands will have subtly different conformations in the separation medium. There are at least three important limitations to the sensitivity of SSCP analysis. First, the "mildly" denaturing condition is not well defined and may have to be optimized for each DNA region. This is because the conformation of each strand, and therefore any changes in conformation, is specific to a particular sequence. Therefore, the mobility differences will not be observed if the separation conditions are not optimized for each particular sequence in the sample. Second, visualization after the separation is complex. For example, the introduction of a radionucleotide probe or a fluorescence label into the DNA strand requires prior knowledge of the specific sequences of DNA regions around the point of mutation. Third, at present the assay is not reliable with fragments greater than around 200 bp and the sensitivity is only 60–95%.

For the analysis of double-stranded DNA, conformation-sensitive gel electrophoresis (CSGE) is possible. This approach is based on slight differences in conformations between the homoduplex and the heteroduplex DNA fragments. Just as discussed for SSCP above, the optimal gel and buffer conditions are particular to each sequence. Only when applied together with SSCP can the mutation detection rate approach 100%.

A different approach is to use denaturing gradient gel electrophoresis (DGGE). Separation is performed at a constant temperature but with a gel constructed to provide various degrees of denaturation along its length. If the sequence is known around the region probed, the mutation detection rate can reach 100%, but irreproducibility in creating identical gels makes implementation difficult. Also, it is often necessary to attach an artificial GC-rich sequence to the respective ends of the two strands to provide optimum separation.

Compared to SSCP or CSGE, DGGE can handle longer DNA fragments and is less time-consuming. An analog of DGGE is temperature-gradient gel electrophoresis (TGGE). In TGGE, instead of a denaturant gradient along the gel, a spatial or temporal temperature gradient is used to perform the same function. A simpler scheme is to apply constant denaturing capillary electrophoresis (CDCE). But this is again limited to defined mutations.

Capillary electrophoresis (CE) provides rapid analysis, a small sample requirement, and high sensitivity. It has been successfully used in many DNA analysis fields like sequencing and genotyping. Recently developed multiple-capillary arrays are ideal for high-throughput analysis. It is possible to detect mutations using CDCE with laser-induced fluorescence of covalent tags or with DGCE using a secondary polymer concentration gradient to refocus the sample band in addition to a denaturant gradient. The construction of gradients in the above techniques are tedious and hard to reproduce, especially for a capillary array.

The temperature of the separation medium within a capillary can be modified internally through ohmic heating by varying the electric potential across the capillary. Limitations of this technique include the narrow temperature range that can be achieved and the mutual dependence of the temperature and the electric field. This dependence is undesirable because the optimal separation conditions for a particular sample may not be achieved at an electric field consistent with heating the capillary to the required temperature.

SUMMARY OF THE INVENTION

An embodiment of the present invention relates to an improved method for detecting mutations in a nucleotide-containing sample by subjecting the sample nucleotides to temperature gradient electrophoresis and obtaining spectroscopic intensity data indicative of the presence of the nucleotides. Preferably, the sample comprises at least one pair of nucleotide sequences. Each member nucleotide sequence is preferably a double strand of DNA. A preferred pair of nucleotides sequences comprises a heteroduplex DNA fragment and a homoduplex DNA fragment. The presence of a mutation is determined by comparing the spectroscopic intensity indicative of the presence of the member nucleotides of a pair.

Another embodiment of the present invention relates to a temperature gradient electrophoresis-based method for generating data indicative of the presence of a single nucleotide polymorphism or a mutation in a biological sample. The sample includes non-desalted polymerase chain reaction (PCR) products. Thus, the biological sample has preferably not been desalted.

A first nucleotide-containing compound having non-desalted polymerase chain reaction (PCR) products and a second nucleotide-containing compound are provided. A preferred nucleotide-containing compound is a DNA fragment. The first and second nucleotide-containing compounds are subjected to temperature gradient electrophoresis to cause the first and second nucleotide-containing compounds to migrate at different relative rates. The first nucleotide-containing compound, which includes non-desalted PCR products are irradiated to generate a first spectroscopic signal. The second nucleotide-containing compound is irradiated with light to generate a second spectroscopic signal.

The spectroscopic signals can be, for example, fluorescence emitted by a DNA staining agent. Alternatively, the spectroscopic signals can correspond to the light used to irradiate the nucleotide-containing compounds. In this case, the presence of the compounds themselves attenuates the light.

The first and second spectroscopic signals are converted into first and second data suitable for determining the presence of a single nucleotide polymorphism or a mutation in the first nucleotide-containing compound. An example of suitable data is an electropherogram indicative of a time record of the spectroscopic signals. Other suitable data include data indicative of the number of peaks or widths of peaks present within a portion of the electropherogram.

Another embodiment of the invention relates to a temperature gradient electrophoresis-based method for generating data indicative of the presence of a single nucleotide polymorphism or a mutation in a biological sample having non-desalted polymerase chain reaction (PCR) products. A first nucleotide-containing compound having non-desalted polymerase chain reaction (PCR) products is provided. The first nucleotide-containing compounds is subjected to temperature gradient electrophoresis. The first nucleotide containing compound is irradiated to generate a first spectroscopic signal, which is converted into first data suitable for determining the presence of a single nucleotide polymorphism or a mutation in the first nucleotide-containing compound. The determination can be made by comparing the first data with reference data, which is preferably obtained by conversion from a second spectroscopic signal, which is obtained by irradiating a second nucleotide containing compound that has been subjected to temperature gradient electrophoresis.

Another embodiment of the invention relates to method for determining the presence of a single nucleotide polymorphism or a mutation in a biological sample having non-desalted polymerase chain reaction (PCR) products. First and second parameters are obtained. The first parameter is representative of a first spectroscopic signal resulting from irradiating a first nucleotide-containing compound having non-desalted polymerase chain reaction (PCR) products that has been subjected to temperature gradient electrophoresis. The second parameter is representative of a second spectroscopic time signal resulting from irradiating a second nucleotide-containing compound that has been subjected to temperature gradient electrophoresis. The first and second parameters are compared to determine whether there is a single nucleotide polymorphism or a mutation in the first nucleotide-containing compound.

In one embodiment, the temperature of the sample nucleotides is actively reduced after the nucleotides are subjected to temperature gradient electrophoresis but prior to obtaining the spectroscopic signals. The active temperature reduction preferably comprises flowing a gas or fluid in thermal contact with the sample nucleotides. The flow is preferably imparted by a fan, pump, or other flow producing device. The rate of flow preferably exceeds the rate of flow that would occur as a result of convective flow alone.

The temperature of the nucleotides is preferably reduced by an amount sufficient to anneal substantially all double stranded nucleotide sequences that were denatured during the temperature gradient electrophoresis. The temperature is reduced to less than about 35° C., preferably less than about 25° C., more preferably less than about 20° C., and most preferably less than about 15°.

The active temperature reduction preferably comprises at least one of using a flowing gas, such as a chilled gas, in thermal contact with the sample nucleotides and using a circulating fluid in thermal contact with the sample nucleotides. By chilled it is meant that the gas has a temperature of less than about 17.5°, preferably less than about 15°, and more preferably less than about 12.5° C.

In another embodiment, the temperature reduction comprises thermoelectrically cooling the sample nucleotides. The thermoelectric cooling can be accomplished using, for example, a Peltier cooler disposed in thermal contact with the sample nucleotides.

In one embodiment, the sample nucleotides are subjected to electrophoresis in the presence of at least one DNA staining dye, such as a fluorescent intercalating dye or dye that interacts non-covalently with the DNA. In a preferred embodiment, first and second nucleotide sequences are subjected to temperature gradient electrophoresis in the presence of at least two different dyes, such as fluorescent dyes that bind covalently to the DNA sequences. Preferably, the dyes fluoresce at each of two different wavelengths to allow the dyes and thus the sequences to be discriminated.

The first and second nucleotide sequences are subjected to temperature gradient electrophoresis, preferably in the same capillary or microchannel. First fluorescence intensity data is obtained at a first wavelength, where the first fluorescence intensity data is indicative of the presence of the first nucleotide sequence. Second fluorescence intensity data is obtained, preferably simultaneously with the first fluorescence intensity data, at a different, second wavelength. The second fluorescence intensity data is indicative of the presence of the second nucleotide sequence.

The presence of mutation in the first nucleotide sequence is determined by comparing the first fluorescence intensity data with fluorescence intensity data indicative of the presence of a third nucleotide sequence, such as a sequence known to be free of mutation. The presence of mutation in the second nucleotide sequence is determined by comparing the second fluorescence intensity data with fluorescence intensity data indicative of the presence of the third nucleotide sequence.

Yet another embodiment of the present invention relates to a method for determining the presence of a single nucleotide polymorphism or a mutation in a biological sample comprising first and second nucleotide containing compounds. A first parameter representative of a first spectroscopic signal resulting from irradiating the first nucleotide-containing compound is obtained. The first compound is irradiated after having been subjected to temperature gradient electrophoresis by changing a temperature at a first rate during the electrophoresis. A second parameter representative of a second spectroscopic signal resulting from irradiating the second nucleotide-containing compound is obtained after the second compound has been subjected to temperature gradient electrophoresis by changing a temperature at a second, different rate during the electrophoresis. The first parameter is compared to a first reference parameter to determine whether there is a single nucleotide polymorphism or a mutation in the first nucleotide-containing compound. The second parameter is compared to a second reference parameter to determine whether there is a single nucleotide polymorphism or a mutation in the second nucleotide-containing compound. Preferably, the first reference parameter is representative of a first reference spectroscopic signal obtained from a reference nucleotide containing compound that had been subjected to electrophoresis by changing the temperature at the first rate. Preferably, the second reference parameter is representative of a second reference spectroscopic signal obtained from the reference nucleotide containing compound after subjecting the reference compound to electrophoresis by changing the temperature at the second rate.

Another embodiment of the invention relates to a temperature gradient electrophoresis-based method for generating data indicative of the presence of a single nucleotide polymorphism or a mutation in a biological sample. The method comprises subjecting the first nucleotide-containing compound to electrophoresis in a micro-channel disposed in a substantially planar substrate. During electrophoresis, a temperature of the first nucleotide-containing compound is changed by an amount sufficient to change an electrophoretic mobility of the first nucleotide-containing compound. Subsequently, the temperature of the first nucleotide-containing compound is thermo-electrically reduced, preferably by a thermo-electric cooler in thermal contact with the micro-channel. The first nucleotide-containing compound is irradiated with light to generate a first spectroscopic signal and the first spectroscopic signal is converted into first data suitable for determining the presence of a single nucleotide polymorphism or a mutation in the first nucleotide-containing compound. A second spectroscopic signal and second spectroscopic data can be obtained by irradiating a second nucleotide containing compound that has been subjected to temperature gradient electrophoresis and thermoelectric temperature reduction. Preferably, the presence of single-nucleotide polymorphism or mutation can be determined by comparing the first and second spectroscopic data or by comparing parameters derived from the spectroscopic data.

In any embodiment of the invention, the sample nucleotides can comprise homoduplex or heteroduplex DNA fragments. In one embodiment, the temperature gradient electrophoresis comprises temporally modifying the temperature of the DNA fragments by an amount sufficient to at least partially denature at least one of the DNA fragments.

The sample nucleotides can be the products of a polymerase chain reaction (PCR). In one embodiment, the PCR products are electrophoresed without having first been desalted. In another embodiment, the PCR products are electrophoresed without single stranded DNA being removed from the PCR products. Thus, the presence of mutation in a double stranded DNA sequence is determined in the presence of single stranded DNA.

In another embodiment, the sample nucleotides are electrophoresed in a capillary, and at least one of a current across the capillary or a resistance through the capillary is substantially constant during the temperature gradient.

In yet another embodiment, the method includes providing a reference sample comprising reference nucleotides, subjecting the reference nucleotides to temperature gradient electrophoresis in the presence of an intercalating dye, obtaining fluorescence intensity data indicative of the presence of the reference nucleotides, and determining the presence of a mutation by comparing the fluorescence intensity data of the unknown nucleotides to the fluorescence intensity data of the reference nucleotides.

The sample and the reference nucleotides are preferably simultaneously electrophoresed in respective, different capillaries. In one embodiment, the reference nucleotides are substantially free of mutation sites. Alternatively, in yet another embodiment, the reference nucleotides comprise at least one mutation.

BRIEF DESCRIPTION OF THE DRAWINGS

The present invention is described in detail below with reference to the drawings in which:

FIGS. 5a and 5b show fluorescence intensity data of a first unknown and a first reference nucleotide-containing compound, respectively;

DETAILED DESCRIPTION OF THE PREFERRED EMBODIMENT

Figure 1A:
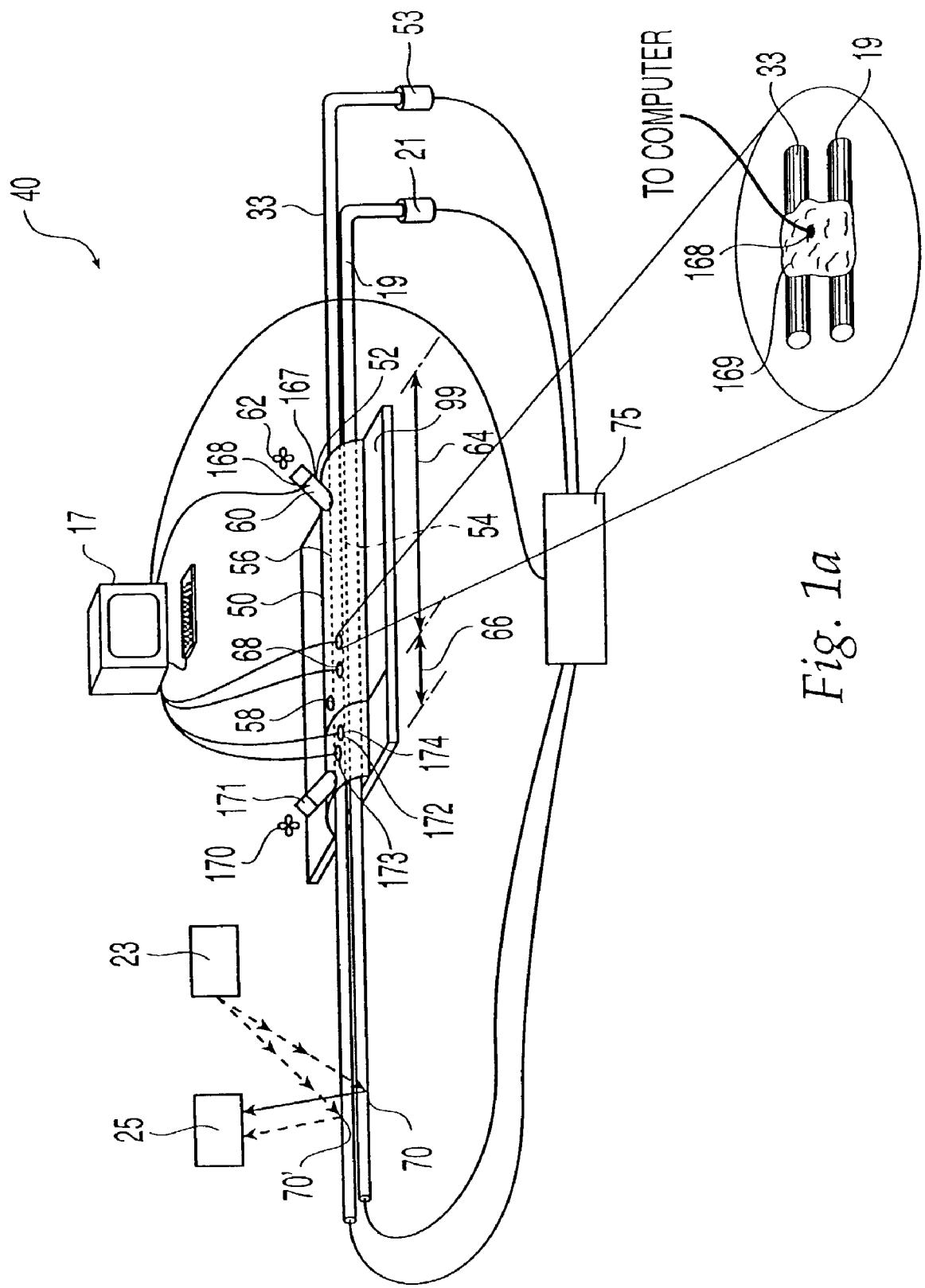
FIG. 1a shows an embodiment of a mutation detection device having a gas cooled portion in accordance with the present invention.

The present invention relates to a rapid method of using capillary electrophoresis for determining the presence of a single nucleotide polymorphism or mutation in a sample, which preferably comprises nucleotides. As used herein, samples refer to samples that have components that are to be analyzed to determine the presence of a single nucleotide polymorphism or mutation therein. In addition to nucleotide containing compounds, such as DNA fragments, the present invention is adaptable to other compounds, such as proteins, peptides, RNA, and the like, having a temperature dependent mobility in the presence of an electric field.

It is understood in the art that a single nucleotide polymorphism (SNP) is an inherited variation in the genome of an individual. Thus, a SNP can be detected by comparing DNA of one individual of a population with DNA of another individual of the population. A mutation, on the other hand, is a change in the genome sequence that results from a perturbation, such as exposure to radiation or a chemical mutagen. A mutation can be detected by comparing DNA of an individual before exposure of the individual to a perturbation with DNA of the individual after exposure of the individual to the perturbation. The present method is equally adapted to determining the presence of SNP's or mutation's. As used herein, it should be understood that the term "mutation" is meant to include variations, such as deletions, insertions, or substitutions, in nucleotide sequences whether those variations result from an external perturbation, such as a mutation, or are inherited, such as SNP's. Thus, the terms "mutation" and "single nucleotide polymorphism" are used interchangeably.

In the method of the invention, a temporal temperature gradient is applied to a temperature controlled zone of an electrophoretic separation medium. During the temperature gradient, each nucleotide in the sample preferably experiences a first temperature where the nucleotide acid is not melted and a second, higher temperature where the nucleic acid is melted. Of course, the first and second temperatures will likely be different for different nucleotides. As used herein, the term melt is synonymous with the term thermally denature. The temperature of the temperature controlled zone preferably changes by at least about 1° C. and more preferably at least about 7.5° C. The temperature of the temperature controlled zone is set with a precision of better than about 0.02° C.

The presence of sample components is determined by obtaining spectroscopic data indicative of the presence of sample components. The spectroscopic data can include, for example, absorbance data or fluorescence data.

In one embodiment, the electrophoretic separation medium comprises an intercalating dye, such as ethidium bromide to allow fluorescence detection of the separated nucleotides. The intercalating dye preferentially allows detection of double stranded DNA as compared to single stranded DNA. In one embodiment, the separation medium is substantially free of a covalent tag suitable for fluorescence detection of single strands of DNA and the separation medium is completely free of a covalent tag. By substantially free it is meant that the presence of any covalent tag suitable for fluorescence detection of single strands of DNA is insufficient to interfere with the detection of sample compounds using fluorescence resulting from the intercalating dye. In one embodiment, the nucleotides to be separated are preferably substantially free of fluorescent dyes that covalently tag single stranded DNA. Multiple samples comprising nucleotides, such as DNA fragments, can be simultaneously analyzed.

In another embodiment, the electrophoretic medium comprises a tagging agent, such as an intercalating tag, having an extinction coefficient that is sufficiently large to allow the presence of the sample components to be determined by detecting the absorbance of the tagging agent.

In another embodiment, the presence of the nucleotides is determined by directly measuring the absorbance of the sample components themselves rather than by measuring the absorbance of a tagging agent.

The fluorescence intensity data is indicative of the presence of mutation in the sample components. By indicative, it is meant that the fluorescence data of the sample components can be compared with fluorescence data obtained from reference sample components to determine the presence of mutation. The presence of mutations are preferably identified by comparing electrophoretic fluorescence intensity data resulting from a heteroduplex nucleotide with electrophoretic fluorescence intensity data resulting from a homoduplex reference nucleotide without prior knowledge of the DNA sequence.

The invention is suitable for high-throughput screening of mutations and single-nucleotide polymorphisms, by multiplexing large numbers of samples. Preferably, at least as many as 96 electrophoretic separations can be simultaneously performed.

Temperature Control

FIG. 1a shows a preferred arrangement of an embodiment of the present electrophoretic mutation detection device 40. A separation lane, such as a sample capillary 33, is provided to electrophoretically separate unknown sample compounds. By separation lane, it is meant any structure configured and arranged to separate a sample using electrophoresis. Preferred structures include capillaries and microfabricated channels. The separation takes place within the internal bores of the capillaries or the interior of the microfabricated channels. As discussed below, the internal bore or interior of the channels are filled with a separation medium suitable for supporting an electrophoretic separation.

Capillary 33 is arranged to be in fluid contact with a sample reservoir 53, which is configured to contain a volume of sample sufficient to perform an analysis. The sample is preferably suspended or dissolved in a buffer suitable for electrophoresis. Examples of suitable sample reservoirs include the wells of a microtitre plate, a vessel configured to perform PCR amplification of a volume of sample, a reservoir of a microfabricated lab on a chip device, and the like.

Mutation detection device 40 is preferably provided with an optional reference capillary 19 configured to simultaneously separate a reference sample comprising reference nucleotides. Reference capillary 19 includes a reference reservoir 21 configured to contain the reference sample. Reference capillary 19 and reference reservoir 21 have the same characteristics as the sample capillary 33 and sample reservoir 53. An optional support 99 is provided to stabilize capillaries 19, 33.

Device 40 includes a power supply 75 for providing a voltage and current sufficient for electrophoretic separation of a sample. The power supply is preferably configured to allow at least one of the current or resistance of the capillary to be monitored during a separation. Preferably, the current or resistance data is received by the computing device 17 to allow the electric potential to be varied to maintain a constant current or resistance. This is discussed in more detail below.

A temperature control zone 50 of sample capillary 33 and optional reference capillary 19 are placed in thermal contact with an external heat source, such as a gas, which is used to heat portions of capillaries 33, 19. Air or nitrogen are examples of gas that can be used. Because the capillaries 33, 19 preferably have a radius of less than about 500 microns, the thermal conductivity between the separation medium within the internal bores of the capillaries and the gas is sufficiently high to allow the gas to heat the separation medium. Thus, during electrophoresis, the external heat source, rather than ohmic heating of the separation medium itself, is the dominant source of any substantial temperature changes or fluctuations within the separation medium within the capillary. Because sample components, such as nucleotides, migrate within the separation medium, which typically contains a liquid, the sample components are also in thermal contact with the external heat source.

Temperature control zone 50 preferably extends for a length $T_{temp}$ 64 of the capillaries. At least one inlet port 52 is provided to introduce the heated gas to a heated region 54 between the capillaries and a thermal jacket 56. At least one outlet 58 is provided to allow the gas to exit from heated region 54. A fan 62 or other device to force the gas into the inlet and out of the exit is provided. Thermal jacket 56, which can entirely surround capillaries 33, 19, insulates temperature control zone 50 to reduce heat loss therefrom and to maintain the gas in contact with capillaries 33, 19.

The gas can be heated by, for example, passing the gas over a resistively heated filament 167 or a heat exchanger prior to introducing the gas into heated region 54. Filament 167 can be located within or adjacent inlet port to reduce heat loss that would occur if hot gas were transported from a location remote from device 40.

At least one temperature sensor 68 is preferably used to determine the temperature of the gas in contact with capillaries 33, 19 in the portion $T_{temp}$. An additional temperature sensor 168 is placed in thermal contact with the capillaries in the portion $T_{temp}$. Preferably, sensor 168 is embedded in a mass of thermally conductive material 169, so that the temperature reported by sensor 168 is indicative of the temperature within the internal bore of capillaries 33, 19. Suitable thermally conductive materials include, for example, the TCE series of thermal epoxies available from Melcor, Trenton, N.J.

A computer 17 receives signals from sensors 68, 168 indicative of the gas temperature, and capillary temperature, respectively. The temperature of filament 167 is preferably under control of computer 17, which is configured to vary the current flowing through the filament. During operation, computer 17 compares the temperature received from sensor 168 (capillary bore temperature) with a predetermined target temperature, which can vary as a function of time. If the capillary bore temperature is less than the target temperature, computer 17 raises the temperature of filament 167, such by increasing the amount of current flowing through filament 167, to increase the gas temperature in contact with capillaries 33, 19. Conversely, if the capillary bore temperature is greater than the target temperature, computer 17 lowers the temperature of filament 167, such by decreasing the amount of current. The difference between the temperature received from sensor 68, which measures the gas temperature, and the temperature from sensor 168 is used to determine relative change in filament temperature that is required to reach the target temperature. For example, if the temperatures of the gas and capillary bores are each significantly less than the target temperature, a greater increase in the filament temperature is required than if only the capillary bore temperature is significantly less than the target temperature.

As an alternative to controlling the gas temperature by varying a filament temperature, the gas temperature can be varied by mixing a first hot gas and a second, cooler gas. By varying the ratio of the gas volumes in the mixed stream, the temperature can be varied. A mass flow controller, such as the Type 1179A General Purpose Mass Flow Controller provided by MKS Instruments of Andover, Mass., can be used to obtain and measure a variable degree of mixing between the two gas sources.

Controlling the temperature of the sample components within the capillary by use of a gas rather than by using a liquid, allows the temperature of the capillary bore (and sample components therein) to be changed much more rapidly because the temperature of the gas can be changed much more rapidly than the temperature of a liquid. It should be understood, however, that, where rapid temperature changes are not required, a liquid may be used to control the temperature of the temperature control zone.

A portion $T_{cool}$ 66 of capillaries 33 and 19 can be provided to reduce the temperature of sample components, such as nucleotides, after the samples have passed through the temperature control zone. Cooling the sample components can provide an increase in detection efficiency, as discussed below. The temperature in portion $T_{cool}$ 66 can be controlled using chilled gas with an arrangement similar to that provided in the temperature control zone. Because the radial dimensions of capillaries 33, 19 are on the order of about 500 microns or less, cooling the capillaries themselves serves to cool sample components migrating within the separation filling the internal bores of the capillaries. Thus, the chilled gas in the portion $T_{cool}$ is in thermal contact with sample components present within the internal bores of capillaries 33, 19.

A fan 170 or other air circulation device is provided to introduce chilled gas into an inlet port 171. Upon entering the inlet port 171, the chilled gas comes into thermal contact with the portions capillaries 33, 19 disposed in $T_{cool}$ and sample components present in the cooled capillary portions. The chilled gas entering input port 171 can be provided by, for example, contacting the gas with a condenser or heat exchanger filled with a chilled liquid. An outlet port 172 allows chilled gas to escape.

A sensor 173 monitors the gas temperature within $T_{cool}$ and a sensor 174, which is in thermal contact with capillaries 33, 19, determines the temperature within the bores of the capillaries. Computer 17 preferably receives signals from sensors 173, 174. As the temperature within the temperature controlled portion of the system increases, additional cooling may be required to maintain a predetermined target temperature within $T_{cool}$. If computer 17 determines that the temperature within $T_{cool}$ is greater than the target temperature, the gas flow rate through $T_{cool}$ can be increased, such as be increasing the fan speed.

Device 40 also includes a light source 23, such as a laser emitting a wavelength suitable to generate fluorescence from the intercalating dye. A detector 25 is arranged to obtain fluorescence intensity data, such as a time-intensity electropherogram including peaks indicative of the presence of nucleotides, and send the detected fluorescence intensities to computing device 17.

Figure 1B:
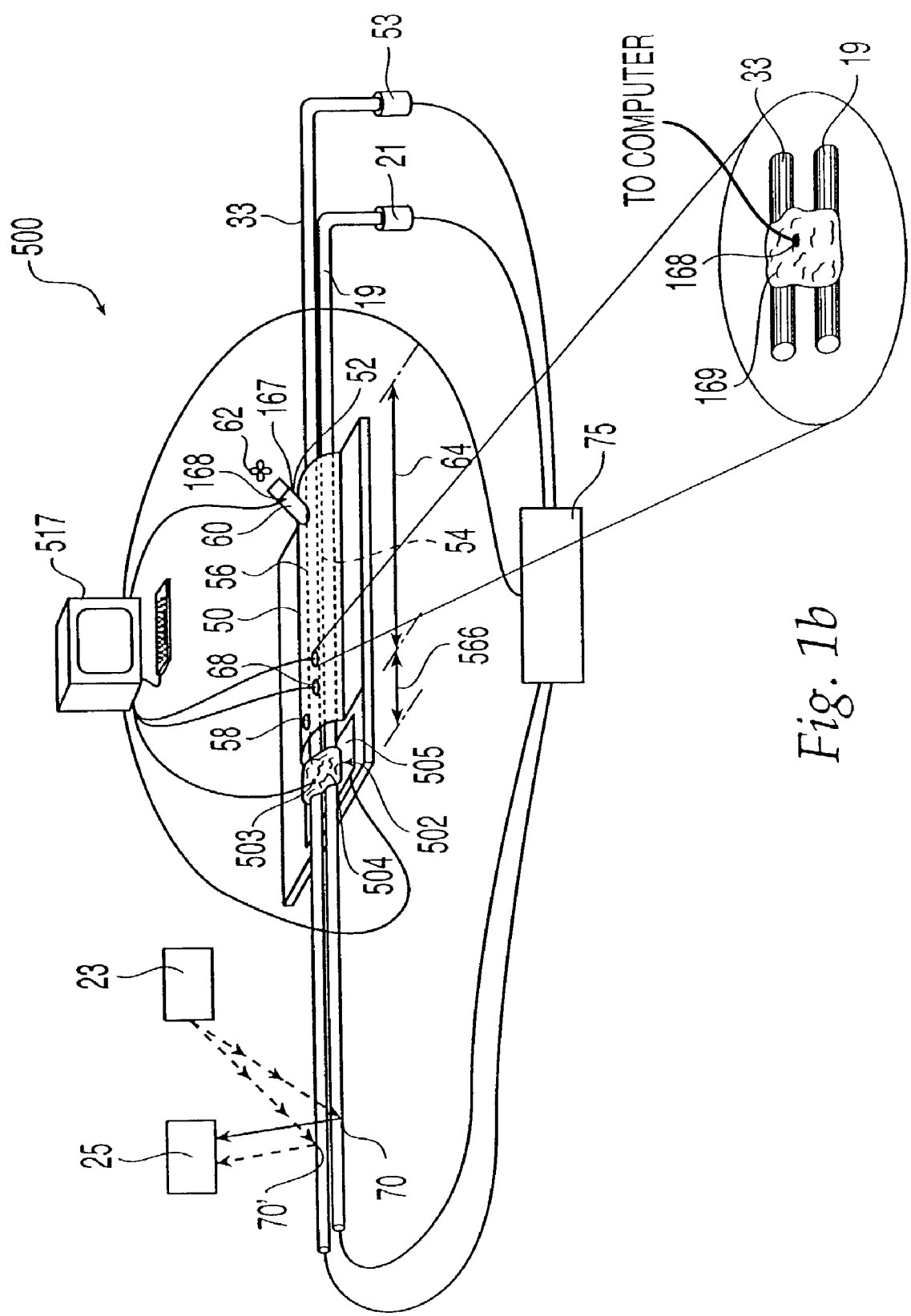
FIG. 1b shows an embodiment of a mutation detection device having a thermoelectrically cooled portion in accordance with the present invention.

Referring to FIG. 1b, a mutation detection system 500 having a thermoelectric cooler, such as a Peltier cooler 502, to cool samples that have been subjected to temperature gradient electrophoresis is shown. An example of a suitable Peltier cooler is the Thermo-Electric Module No. 01/128/040 available from Ferrotec America Corporation, Nashua, N.H. Peltier cooler 502 cools at least a portion of capillaries 33, 19 disposed in a cooled portion $T_{cool}$ 566. A chilled side 505 of Peltier cooler 502, which is controlled by computer 517, is disposed in thermal contact with a portion of capillaries in $T_{cool}$. By cooling a portion of capillaries 33, 19, cooler 502 also cools samples within the cooled portions of the capillaries. As understood in the art, Peltier coolers release heat on a side that opposes the chilled side. Thus, device 500 preferably includes an apparatus, such as for circulating water or flowing gas, to remove heat from the Peltier cooler.

Thermal contact between Peltier cooler 502 and capillaries 33, 19 is preferably enhanced by using a thermally conductive material, such as a thermal paste 504, which surrounds a portion of the capillaries in contact with Peltier cooler 502. Computer 17 receives signals from a temperature sensor 503 indicative of the temperature within the internal bore of capillaries 33, 19. Computer 17 can vary the cooling level of Peltier cooler 502 by varying the current supplied to the device, as understood in the art. During operation, computer 17 compares the temperature determined by sensor 503 with a predetermined target temperature and increases or decreases the cooling level of Peltier cooler 502 if the temperature is too high or low, respectively.

Figure 1C:
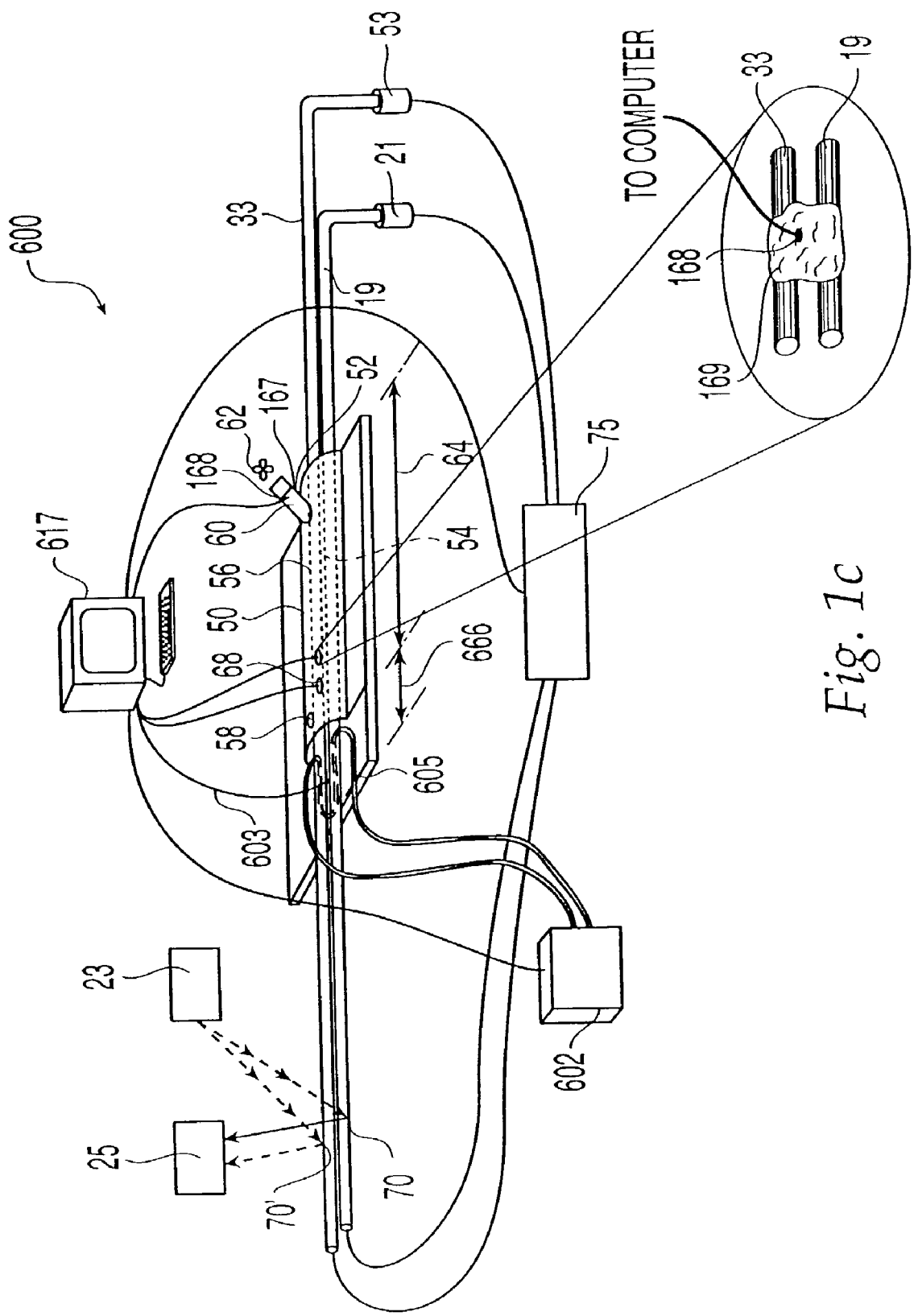
FIG. 1c shows an embodiment of a mutation detection device having a liquid cooled portion in accordance with the present invention.

Referring to FIG. 1c, a device 600 having a liquid chiller 602, is shown. An example of a suitable chiller is the MLA270 Series chiller available from Melcor, Trenton, N.J. Liquid chiller 602, which is under the control of a computer 617, circulates a chilled liquid, such as water, a poly-alcohol, or mixture thereof, through tubing 605, which is in thermal contact with the portions of capillaries 33, 19 disposed in portion $T_{cool}$ 666. Computer 617 receives signals from a temperature sensor 603 disposed in thermal contact with capillaries 33, 19 in portion $T_{cool}$. When the temperature indicated by sensor 603 deviates from a predetermined target temperature, computer 617 instructs chiller 602 to decrease or increase the temperature of the liquid flowing through tubing 605 depending upon whether the sensor 603 temperature is too high or low, respectively.

The temperature and length of portions $T_{cool}$ 66, 566, 666, hereinafter referred to collectively as $T_{cool}$, are preferably low enough and long enough, respectively, to allow DNA fragments that are thermally partially denatured within temperature control zone 50 to anneal prior to being detected at a reference detection zone 70 or a sample detection zone 70'. Because the system preferably uses an intercalating dye that is selective for double stranded DNA fragments, allowing denatured fragments to substantially re-anneal enhances the detection sensitivity. The temperature of $T_{cool}$ is reduced to less than about 35° C., preferably less than about 25° C., more preferably less than about 20° C., and most preferably less than about 15°.

In any embodiment of the present invention, the fluorescence intensity data of the unknown sample is preferably obtained simultaneously with the fluorescence intensity data of the reference sample. By "simultaneously," it is meant that the unknown and reference samples are electrophoresed in a total time that is at least about 25% less, preferably about 50% less, than twice the time required to sequentially electrophorese the samples. Preferably, the unknown sample is subjected to capillary electrophoresis in the sample capillary and the reference sample is subjected at substantially the same time to capillary electrophoresis in a second, different capillary.

Sample components, such as first and second pairs of nucleotides, can be subjected to temperature gradient electrophoresis in the presence of more than one DNA staining dye. The different intercalating dyes preferably fluoresce at wavelengths that are sufficiently different to allow the presence of one of the dyes to be detected even when the other dye is also present. To simultaneously detect fluorescence from each of two or more dyes, the mutation detection detector preferably comprises a light dispersing element, such as a grating or prism, and a two-dimensional detector, such as a charge coupled device. An example of a suitable detector is described in U.S. Pat. No. 6,118,127, which is incorporated herein to the extent necessary to understand the present invention.

Each pair of nucleotides that are separated in the presence of the two intercalating dyes comprises two member nucleotides. Each member nucleotide is preferably a double stranded nucleotide, such as a heteroduplex or homoduplex DNA strand. Preferably, one of the intercalating dyes interacts preferentially with the first pair of nucleotides and the second intercalating dye interacts preferentially with the second pair of nucleotides. Thus, it is possible to determine the presence of both members of each of the first and second pairs of nucleotides even if the pairs do not become spatially resolved during electrophoresis.

Separation Media

A preferred separation medium for mutation detection comprises a buffer, such as 1×TBE buffer, which can be prepared, for example, by dissolving 8.5 g premixed TBE buffer powder (Amerosco, Solon, Ohio) into 500 ml dionized water. An intercalating dye, such as Ethidium bromide is incorporated into the TBE buffer at a concentration sufficient to provide detection of double stranded DNA in the sample. The suitable dye concentration depends upon the particular sample and can be determined by, for example, varying the dye concentration in a series of standard samples to obtain a calibration curve of intensity versus dye concentration. As an alternative to an intercalating dye, a dye that covalently binds to the DNA can be used. An intercalating dye is preferred, however, at least because the intercalating dye can be added to the running buffer. Thus, a separate step to tag the strands of DNA is not required.

The present invention preferably allows mutation detection of DNA fragments from PCR products without first desalting or substantially purifying the products, such as by a filtration or pre-separation. In particular, the present method can be performed without removing single stranded DNA from the PCR products. This is especially important in mutation detection because the samples usually contain other biological tissues, cells, or reagents. Thus, memory effects and impurities are more of a concern in mutation detection as opposed to DNA sequencing. Sampling PCR reaction products, which may contain single strand sequences of DNA, without first desalting or purifying the products is made possible at least in part by the use of an intercalating dye, which preferably associates selectively with double stranded DNA rather than single stranded DNA. The PCR products would have to be depleted of single stranded DNA if traditional dye labels were used because the fluorescence signals from the labeled single strands would interfere with detection of the desired double stranded fragments.

Additionally, the present mutation detection device is preferably configured to inject a high pressure fluid through each separation capillary to reduce memory effects from previous analyses.

A sieving matrix can be prepared using Polyvinylpyrrolidone (PVP) which is available from Sigma (St. Louis, Mo.). A preferred sieving matrix can be made by dissolving about 0.5% to about 6% (w/v) of 360,000 M PVP into 1×TBE buffer with the intercalating dye. Preferably, the amount of PVP is about 3% (w/v). The viscosity of a three percent solution is less than 10 cp. The use of polyvinylpyrrolidone makes the capillary regeneration process very easy to implement. The capillaries have a negligible failure rate even over several months. The excellent EOF suppressing effect of the PVP medium enhances the reproducibility of decreases uncertainty associated with mutation detection. Alternatively the separation medium includes other sieving matrices such as polyacrylamide gels.

Generating a Temperature Profile

Figure 2:
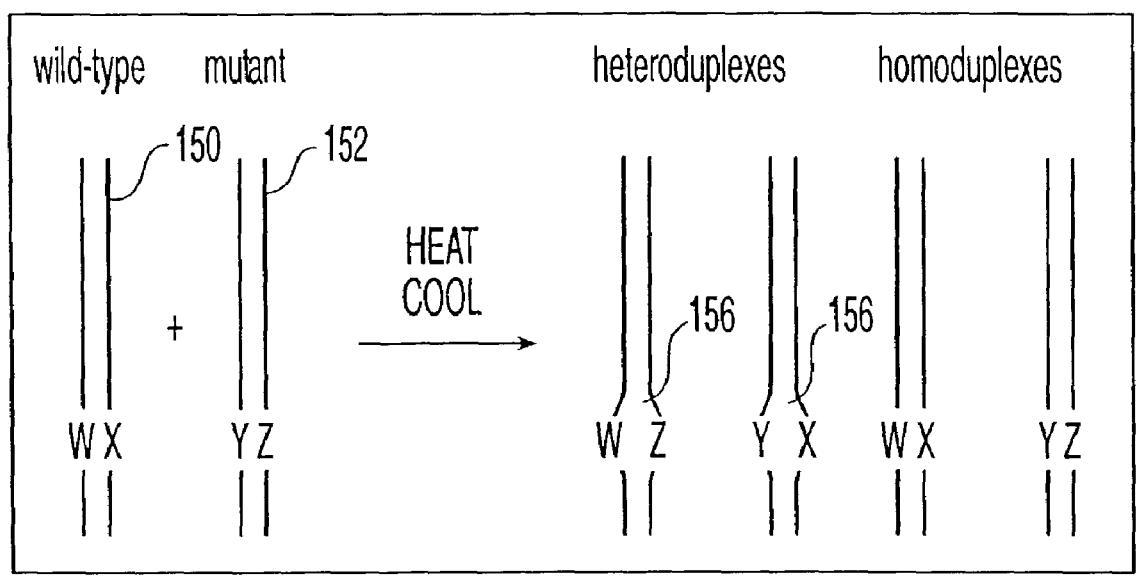
FIG. 2 shows heteroduplex and homoduplex fragments.

FIG. 2 illustrates the creation of a mixture of heteroduplexes and homoduplexes by hybridization. Individuals who are heterozygous in a mutation or polymorphism may have a 1:1 ratio of wild-type 150 and mutant DNA 152. The letters w, x, y, and z indicate arbitrary bases in the DNA strands. As an initial step in determining the presence of a mutation, DNA to be analyzed for the presence of an mutation is preferably mixed with wild-type DNA and hybridized. A mixture of heteroduplexes and homoduplexes is formed when DNA derived from an individual having two mutant alleles (homozygous mutation) is amplified.

However, DNA from homozygous wild-type individuals will form only one species, the homoduplex wild type. Thus, the presence of mutations in an individual's DNA can be detected by determining whether PCR products derived from the individual's DNA comprise heteroduplexes. Using a temperature profile of the present invention, the presence of heteroduplexes can be determined.

In a sample containing both a heteroduplex and the corresponding homoduplex, the heteroduplex will melt (denature) at a lower temperature because the heteroduplex contains a base-pair mismatch. Melting occurs because the thermal energy of the separation medium is sufficient to overcome at least some interaction forces between a pair of DNA strands, at least partially denaturing the DNA. When the DNA becomes partially denatured, the mobility of the partially denatured strands decreases in comparison to a pair of equal length strands that are not denatured to the same extent. Therefore, the heteroduplex can be differentiated from the homoduplex by subjecting a sample to separation at a temperature sufficient to melt the heteroduplex but not the homoduplex.

During a separation performed with a ramped temperature profile, the temperature of the separation medium is increased from an initial value that is less than the melting temperature of both the homoduplex and the heteroduplex. As the temperature is raised, the heteroduplex exhibits a retarded migration behavior near its melting temperature compared to the homoduplex. Thus, the two species begin to separate. As the temperature is raised above the melting temperature of the homoduplex, the homoduplex also denatures and the difference in mobilities between the pair of compounds is reduced. Thus, the extent of separation between a homoduplex and heteroduplex depends in part on the total amount of time the separation medium is at a temperature above the melting point of the heteroduplex but less than the melting temperature of the homoduplex. The mutation can be identified by the difference in the resulting electrophoretic patterns between the homoduplex and the heteroduplex.

A temperature profile of the invention preferably includes at least one change in the temperature of the separation medium as a function of time. Temperatures during the temperature profile can be varied over any time and temperature range sufficient to induce a mobility differential between samples to be separated. In some cases, the analysis objective is to determine if any mutations are present in a sample and the melting temperatures of any heteroduplex-homoduplex pairs that would indicate presence of a mutation are not known before the analysis. Here, the temperature is preferably ramped over a wide range that encompasses the melting temperatures of substantially all heteroduplex-homoduplex pairs that might be present in the sample. In other cases, the analysis objective is to determine whether a sample contains a mutation of a particular type. In this situation, the melting temperatures of a heteroduplex-homoduplex pair that would be indicative of the mutation, if present, are known. As discussed below, the slope of the temperature profile can be optimized to enhance detection of predetermined mutation.

During electrophoresis, the temperature is preferably above the freezing point of the separation medium, such as above about 0° C., and below the boiling point of the separation medium, such as below about 100° C. The temperature within the temperature control zone is preferably substantially constant along a dimension of the separation medium that is perpendicular to the direction of migration. Thus, for example, the temperature is substantially constant across the radial dimensions of a capillary. By substantially constant temperature it is meant that the spatial temperature variations are insufficient to introduce measurable mobility variations for compounds disposed at different spatial locations within the temperature control zone at any given instant. Thus, at any given instant, the temperature at any point along the portion of each capillary within the temperature control zone is preferably constant, i.e., there are substantially no spatial temperature gradients in the temperature control zone.

For accurate comparison of the patterns, a reproducible temperature profile is required. Because in this invention the temperature of the separation medium can be varied independently of the electric field, arbitrary temperature profiles can be selected without negatively perturbing mutation detection performance. For example, for the separation of heteroduplex sample compounds using an apparatus and temperature profile of the present invention, migration times have a relative standard deviation of less than 2%.

Because the mobility retardation (differential mobilities between a heteroduplex and corresponding homoduplex) occurs only when the DNA fragments begin to melt, the part of the capillary that is not elevated above the melting temperature of a fragment, will not affect the differential mobility of the fragments. Preferably, a temperature profile of the invention is not begun until at least some and preferably substantially all fragments in a sample have migrated into the temperature control zone.

In order to generate a reasonably accurate range over which to vary the temperature and the rate of temperature variation, the configuration of the capillary layout has to be considered. Preferably, the temperature range and variation rate are appropriate to allow determination of substantially any mutation in any of the unknown samples being analyzed.

Parameters for a temperature ramping profile preferably include the (1)temperature ramping range from a low temperature $T_L$ to a higher temperature $T_H$; (2) time, $t_r$, after injection at which the temperature ramp is initiated; and (3) rate, r, at which the temperature is ramped.

Preferred procedures for determining temperature ramping parameters include (1) selection of the separation voltage and (2) selection of a sample standard that includes DNA fragments covering the size range of fragments in the samples to be analyzed. The voltage depends on the sieving matrix used, the sizes of the fragments to be separated, and the length of the separation lane, as understood in the art.

The sample standard can be a molecular ladder, mutation standards comprising a particular set of fragments, or a combination thereof. The sizes of the fragments range from the smallest fragment $F_S$ to the largest fragment $F_L$.

Figure 3:
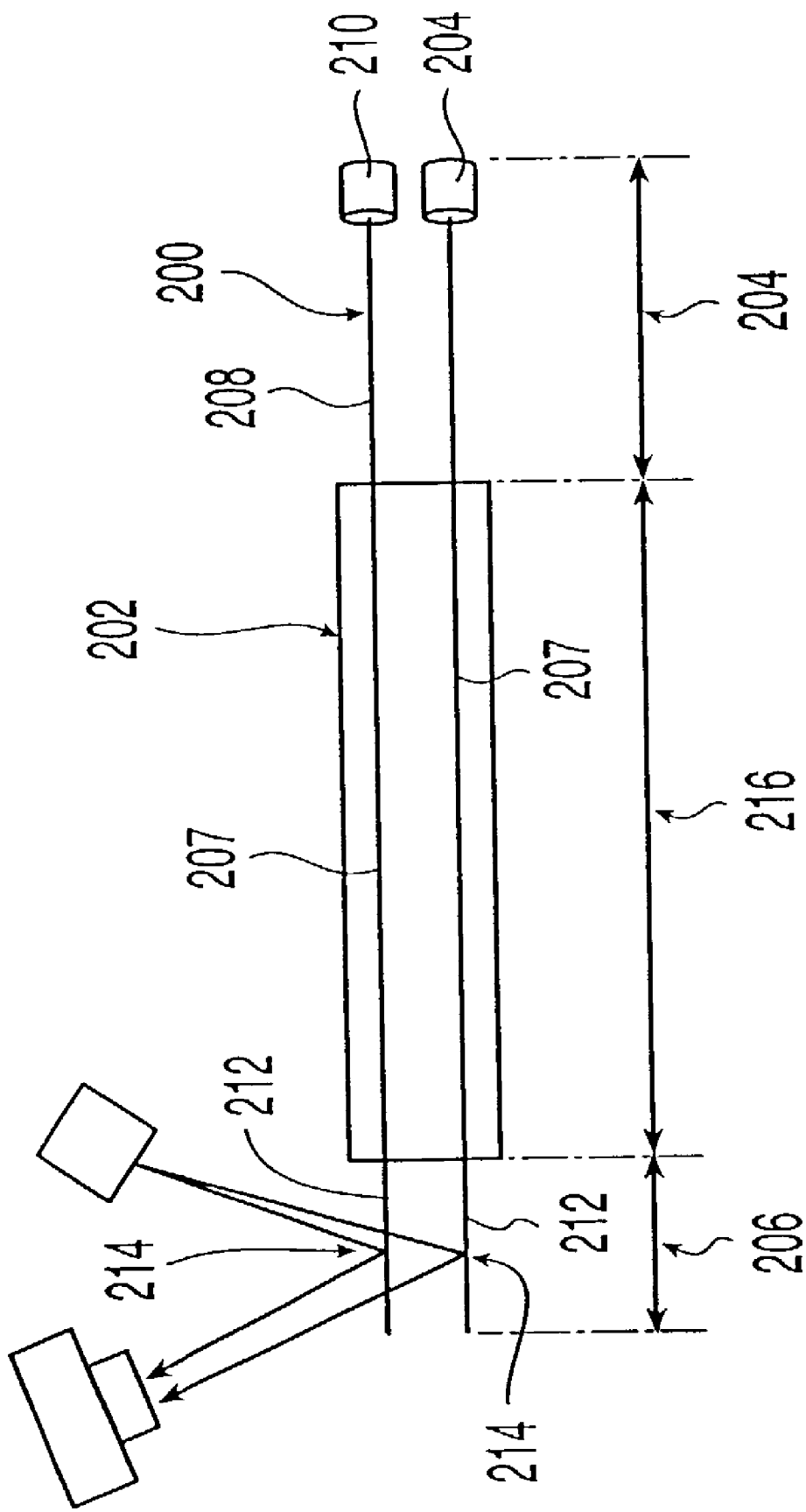
FIG. 3 shows another embodiment of a mutation detection device in accordance with the present invention.

Referring to FIG. 3, an arrangement of multiple capillaries 200 extending through a temperature controlled zone 202 is shown. Capillaries 200 preferably include at least three portions: a first capillary portion 208 preferably extending from a sample injection site 210, a second capillary portion 207 arranged within temperature control zone 202, and a third capillary portion 212 comprising a portion of the capillary between temperature control zone 202 and a detection zone 214. First capillary portion 208 has a length $L_{inj}$ 204 between the sample injection site and the temperature control zone. Second capillary portion 204 has a length $L_{temp}$ 216 within the temperature control zone. Third capillary portion 212 has a length $L_{det}$ 206 between temperature control zone 202 and detection zone 214.

The internal bores of capillaries 200 preferably comprise a separation medium such as polyvinylpyrolidine to provide separation of DNA fragments. The separation medium preferably contains at least one intercalating dye. An electric field sufficient to electrophoretically separate sample compounds within capillaries 200 is applied at least from sample injection sites 210 to detection zones 214. Sample compounds are preferably introduced (injected) at sample injection sites 210 and migrate under the influence of the electric field through capillary portions 208, 207, and 212, before being detected at detection zone 214. Detection of separated sample compounds is preferably by fluorescence detection of the at least one intercalating dye.

When using the present invention to detect a mutation, the temperature of the temperature control zone is preferably not modified until all of the species to be separated have entered temperature control zone 202. To determine the time required for all of the sample compounds to enter temperature control zone 202, a standard sample is preferably run first at the temperature $T_{inj}$ at which $L_{inj}$ will be maintained during the temperature profile. The standard sample preferably comprises fragments having a size range that spans the expected range of fragment sizes in the unknown sample. The migration time, $t_{Tinj, FL}$, for the fragments $F_L$ at the large end of the range of fragment size envelop is determined. The largest fragments are typically the slowest moving fragments and have the longest migration times. The migration time is the time required for the sample to migrate from the injection site 210 to the detection zone. Therefore, the time $t_L$ required for the largest fragment FL to enter the temperature control zone is given by:

$$t_L = \frac{L_{inj}}{L_{inj} + L_{temp} + L_{det}} t_{Tinj,FL}$$

After a time $t_L$, the largest (slowest) fragments in the sample will have entered the temperature-controlled zone.

The length of time for the temperature to ramp from the lowest temperature $T_L$ to the highest temperature, $T_H$, is also determined. The highest temperature is preferably reached before all of the sample compounds have exited the temperature control zone. The sample standard is run with the temperature control zone set to the highest temperature $T_H$. The migration time $t_{TH, FS}$ for the smallest fragment FS is obtained. The shortest time $t_H$ required for the smallest fragment to exit the temperature controlled region with the temperature set at $T_H$, can be estimated as $$t_H = \frac{L_{inj} + L_{temp}}{L_{inj} + L_{temp} + L_{det}} t_{H,FS}$$

For a temperature profile having a single slope, the temperature ramping rate, r, is given by $$r = \frac{T_H - T_L}{t_H - t_L}$$

If the temperature ramping is started right after injection, i.e., before the DNA samples enter the controlled-temperature zone, a ramp beginning at a lower temperature is required to compensate for the temperature ramping that occurs when the sample components are still in the zone of $L_{inj}$. Thus, the starting temperature $T_L'$ of the low end of the temperature ramp can be estimated as:

$$T_L' = T_L - r t_{T_{inj}FL}$$

As an example of determining a temperature profile, assume a sample containing DNA fragments ranging from 200 to 500 bp and a capillary having a total length $L = L_{inj} + L_{temp} + L_{det} = 4.5$ cm + 40.5 cm + 10.0 cm = 55.0 cm When run at an electrical potential of 10 kV and 35° C. constant temperature, the migration time $t_{H, FS}$ for the 200 bp and 500 bp fragments is about 36 and 55 minutes, respectively. The time $t_L$ start the temperature ramping for the controlled-temperature zone can be estimated as:

$$t_L = \frac{L_{inj}}{L_{inj} + L_{temp} + L_{det}} t_{35C,FL} = \frac{4.5 \text{ cm}}{55.0 \text{ cm}} \times 55 \text{ min} = 4.5 \text{ min}$$

When run at 10 kV and 60°, the migration time for the 200-bp DNA fragment is about 27 min. The time for the 200-bp fragment to exit the controlled-temperature zone can then be determined as:

$$t_H = \frac{L_{inj} + L_{temp}}{L_{inj} + L_{temp} + L_{det}} t_{60,FS} = \frac{45 \text{ cm}}{55 \text{ cm}} \times 27 \text{ min} = 22 \text{ min}$$

The rate for temperature ramping from 57° to 65° is then estimated as:

$$r = \frac{T_H - T_L}{t_H - t_L} = \frac{65° \text{ C.} - 57° \text{ C.}}{22 \text{ min} - 4.5 \text{ min}} = 0.46° \text{ C./min}$$

If the temperature ramp of the temperature control zone is begun when the samples are injected, which is before the samples enter the temperature control zone, the actual starting temperature of the temperature control zone is given by:

$$T_L' = T_L - r t_L = 57° - \frac{0.46° \text{ C.}}{\text{min}} 4.5 \text{ min} = 55° \text{ C.}$$

Therefore, the temperature ramping profile would be 55° C. to 65° C. over 22 minutes beginning immediately upon the initiation of electrophoresis.

Figure 4:
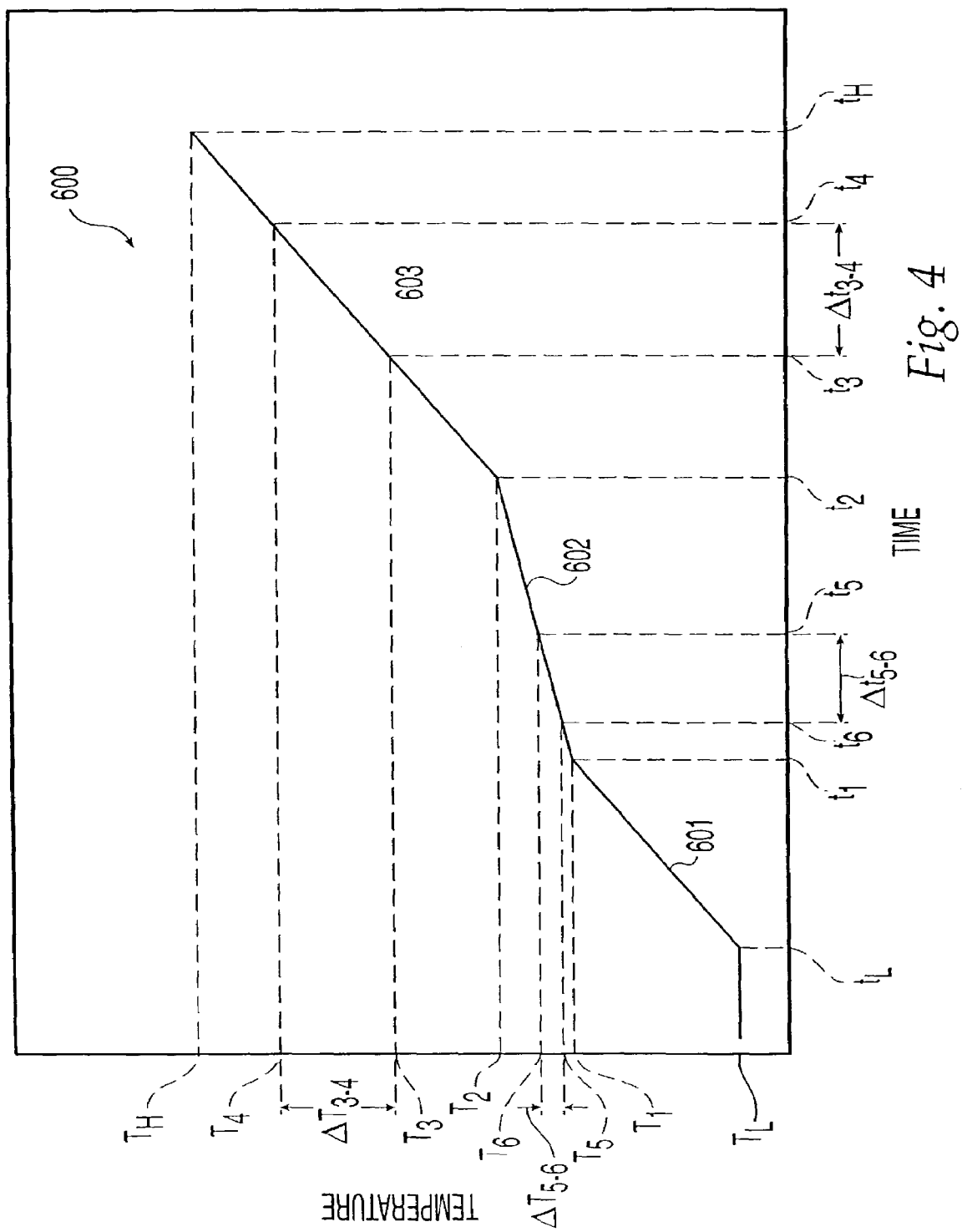
FIG. 4 illustrates a temperature-time profile having a three different ramp periods according to the invention.

Referring to FIG. 4, a temperature profile 600 having ramp periods with different slopes can provide increased ability to detect mutations in complex samples. Temperature profile 600 allows the same or better mutation detection efficiency to be obtained in less than the time required to achieve the same performance using a temperature profile having a single slope. Profile 600 includes 3 temperature ramping periods, although more or fewer ramping periods can be used. Each profile represents the time-changing temperature of sample components present in a temperature control zone.

During a first ramp 601, the temperature of sample components present in the temperature control zone increases from a temperature $T_L$ to a temperature $T_1$. Ramp 601 lasts from a time $t_L$ to a time $t_1$. During a second ramp 602, the temperature of sample components present in the temperature control zone increases with a smaller slope from temperature $T_1$ to a temperature $T_2$. Ramp 602 lasts from time $t_1$ to a time $t_2$. During a third ramp 603, the temperature of sample components present in the temperature control zone increases from temperature $T_2$ to a temperature $T_H$. Ramp 603 lasts from a time $t_2$ to a time $t_H$.

To illustrate how temperature profile 600 improves mutation detection performance over a single slope profile, consider a sample having a first heteroduplex-homoduplex pair comprising a first heteroduplex that melts at a temperature $T_3$ and a first homoduplex that melts at a higher temperature $T_4$ and a second heteroduplex-homoduplex pair comprising a second heteroduplex that melts at a temperature $T_5$ and a second homoduplex that melts at a higher temperature $T_6$. Recall that a heteroduplex-homoduplex pair will exihibit different mobilities if the extent of denaturation (melting) of the members of the pair are different.

During a separation, the first pair will exhibit different mobilities between time $t_3$, when the temperature is $T_3$, and a time $t_4$, when the temperature is $T_4$. Because the temperature melting point differential $\Delta T_{4-3}=|T_4-T_3|$ of the first pair is large compared to the range of ramp 600, the first pair exhibits different separation mobilities over a time differential $\Delta t_{4-3}=|t_4-t_3|$, which is large compared to the length of ramp 600. The $\Delta T$'s are expressed in terms of absolute value because temperature ramps having negative slopes can be used to temperature ramps having positive slopes. Therefore, peaks indicative of the presence of the first heteroduplex and first homoduplex should be well resolved and the presence of the corresponding mutation will not be missed.

The melting point temperature differential $\Delta T_{5-6}=|T_6-T_5|$ of the second pair, however, is much less than the melting point temperature differential $\Delta T_{4-3}$ of the first pair. Thus, if the slope of ramp 602 were as large as the gradient of ramp 603, the second pair would exhibit differential mobilities only over a narrow range of time and might not be resolved. In FIG. 4, however, ramp 602 has a smaller slope than ramp 603, which compensates for the smaller melting point differential of the second pair. Thus, the second pair exhibits differential mobilities over a time differential $\Delta t_{5-6}$, which is sufficiently large to obtain resolution of the member strands of the second pair.

Using multiple slope profile 600 reduces analysis time because if the entire profile had the same smaller slope as ramp 602 a longer period of time would be required to cover the entire temperature range between $T_L$ and $T_H$.

A multiple slope profile, such as profile 600, can also improve analysis in other situations. For example, if a sample includes a plurality of fragments that are closely spaced in size so that they exhibit similar mobilities, the slope of the temperature profile can be decreased over a temperature range corresponding to the melting temperatures of the closely spaced fragments. Because of the decreased slope, each heteroduplex and its corresponding homoduplex in the sample will be exposed to a temperature sufficient to melt the heteroduplex but not the homoduplex for a longer period of time. The heteroduplex and homoduplex experience a differential mobility for a longer period of time.

The times at which to initiate and end a given ramp can be determined in several ways. For example, in many mutation analyses, the melting temperatures of target species, such as a heteroduplex-homoduplex pair, in the sample is known before the analysis is performed. In repetitive analyses, such as clinical assays, the presence of particular target species or the presence of a plurality of closely spaced fragments may also be known prior to the analysis. In these situations, the lower temperature of the ramping period having the lower slope should be lower than the melting temperature of the heteroduplex and the upper temperature of the lower slope ramping period should be higher than the homoduplex.

In one embodiment of the multiple slope temperature ramp, the sample components are subjected to the multiple slope temperature profile during a single electrophoresis run. By electrophoresis run, it is meant an electrokinetic separation that includes the injection, separation, and detection of sample components. Thus, substantially all of the sample components experience both the lower slope temperature ramp and the higher slope temperature ramp. In a different embodiment, the sample components are subjected to temperature gradient electrophoresis, wherein the temperature is changed at a first rate during a first electrophoresis run. During a second electrophoresis run, the sample components are subjected to temperature gradient electrophoresis wherein the temperature is changed at a second, different rate. The first and second electrophoresis runs may be performed sequentially in the same separation lane, such as a capillary or microchannel, or simultaneously in different capillaries or microchannels.

The temperature profile does not have to begin at a lower temperature and increase to a higher value. In one embodiment, a ramp, either linear or non-linear, has a negative slope beginning at a higher temperature and decreasing to a lower temperature while the sample compounds are present in the temperature control zone.

Additionally, more than one temperature profile can be run while a set of sample compounds are present in the temperature control zone. For example, rather than using a single temperature profile that ramps from 60 to 70° C., a set of N temperature ramps can be performed. Preferably, each of the N temperature ramps would range from 60 to 70° C. and back to 60° C. Compared to a single temperature ramp that lasts for a time ts, each of the N temperature ramps would preferably last for a time ts/N. Therefore, if the time ts is less than the time for a given heteroduplex/homoduplex pair to migrate through the temperature control zone, the pair would experience a differential mobility for the same length of time. Each heteroduplex/homoduplex pair comprises two member nucleotides, preferably a heteroduplex double strand of DNA and a homoduplex double strand of DNA.

When different portions of a capillary are at different temperatures, the voltage drop along the capillary is not uniform. Therefore, an electric field correction is preferably made to maintain constant mobilities in the portions $L_{inj}$ and $L_{det}$. This correction increases the precision of the observed migration times. Because the conductivity of the capillary portions outside the temperature control zone is independent of temperature within the temperature control zone, the electric field across the capillary should be proportional to the current through the capillary. When performing a temperature profile, the current across the capillary is preferably maintained at the same amperage as the current that was used in running the standard samples as described above. By adjusting the current across the capillary to have the same amperage during the temperature profile, the DNA mobility outside $L_{temp}$ should be the same regardless of the temperature of $L_{temp}$. A similar correction could be obtained by maintaining a constant resistance across the capillary during a temperature profile.

It should be emphasized that temperature profiles suitable for use with the mutation detection device do not have to be a linear function of time but may also be non-linear or include a combination of profile segments that each have a same or different temperature gradient and duration.

Detection of Mutations

FIGS. 5a and 5b show the fluorescence-migration time data (electropherograms) of two homoduplex samples and the corresponding heteroduplex samples. In these examples, the heteroduplex samples represent unknown samples. As used herein, the term unknown sample indicates a sample that is to be analyzed to determine or confirm the presence of a mutation in the sample. The homoduplex samples serve as reference samples. Upon comparing the spectroscopic signals or data derived from the spectroscopic signals obtained from the unknown sample with that of the reference sample, it is possible to determine or confirm the presence of mutation in the unknown sample.

It should be understood that the reference sample does not have to be electrophoresed simultaneously with the unknown sample. Indeed, the spectroscopic data of the unknown sample can be compared with stored reference data, such as data present in a look-up table or other database. For example, the stored reference data can comprise spectroscopic data derived from one or more reference samples that had been previously subjected to temperature gradient electrophoresis.

Referring to FIGS. 5a and 5b, fluorescence intensity data 300 of an unknown sample includes multiple peaks 302 that do not appear in the fluorescence intensity data of the homoduplex reference sample 304. Extra peaks 302 appear within a migration time $\tau_1$ and a migration time $\tau_2$. The time between migration time $\tau_1$ and migration time $\tau_2$ is a migration time window $w_1$.

Figures 5C, 5D:
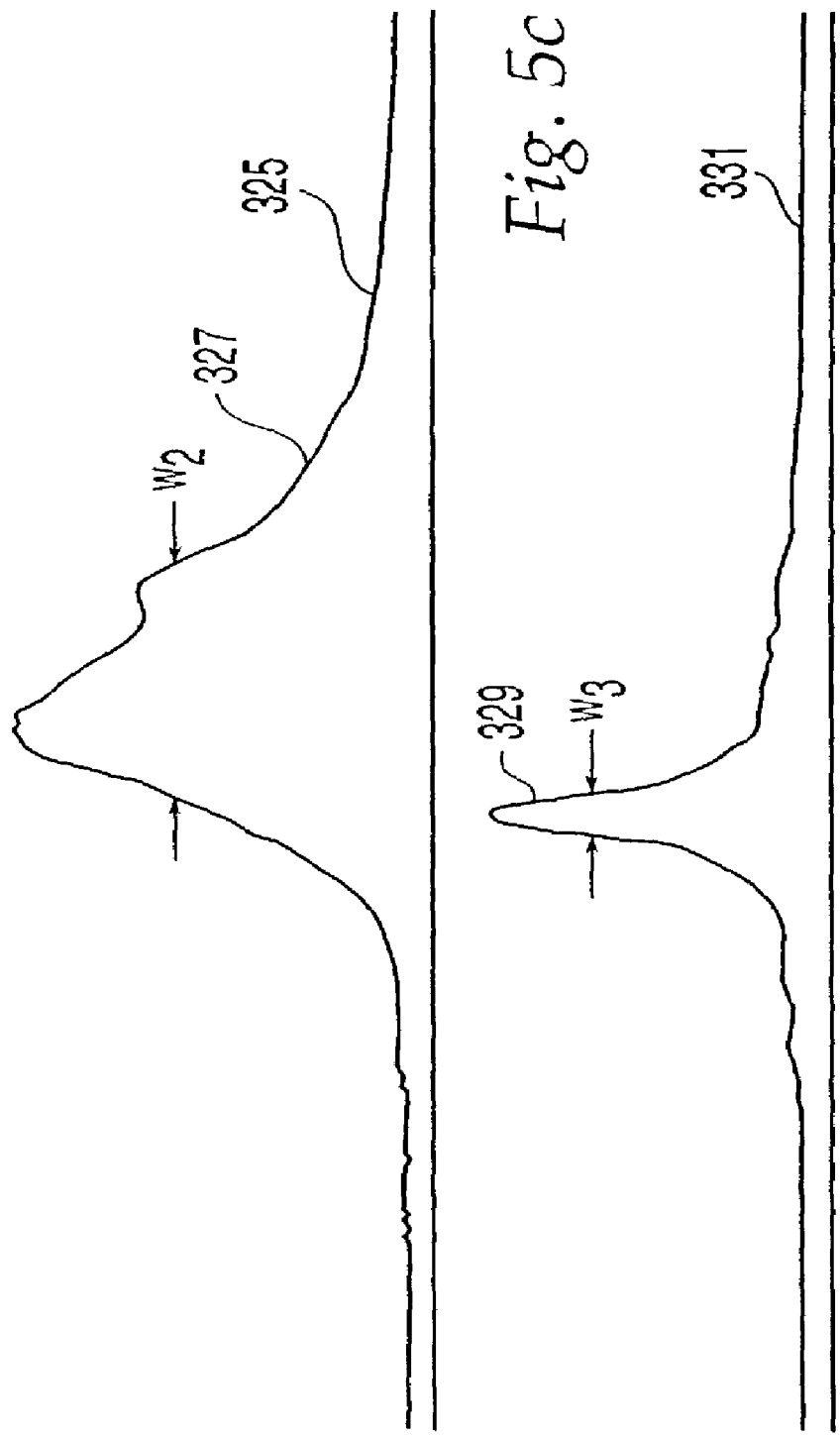
FIGS. 5c and 5d show fluorescence intensity data of a second unknown and a second reference nucleotide-containing compound, respectively.

Referring to FIGS. 5c and 5d, even a slight change in the pattern of peaks is sufficient to be indicative and determinate a mutation in the unknown sample since the present invention provides a highly reproducible system. Perfect separation of the fragments in the heteroduplex samples is not necessary to identify the presence of a mutation. For example, the presence of a mutation in the fluorescence intensity data 325 of the unknown nucleotides shown in FIG. 5c is evident upon comparing data 325 to the reference data 331 even though a peak 327 of the data 325 is not clearly resolved into its 4 components. In this case, the presence of a mutation is determined because peak 327 has a width $w_2$ that is much broader that a width $w_3$ of a peak 329 observed in the fluorescence intensity data 331 of the reference sample, which is free of a mutation. The peak widths are preferably determined at 50% half-maximum intensity, as understood in the art.

Figure 6:
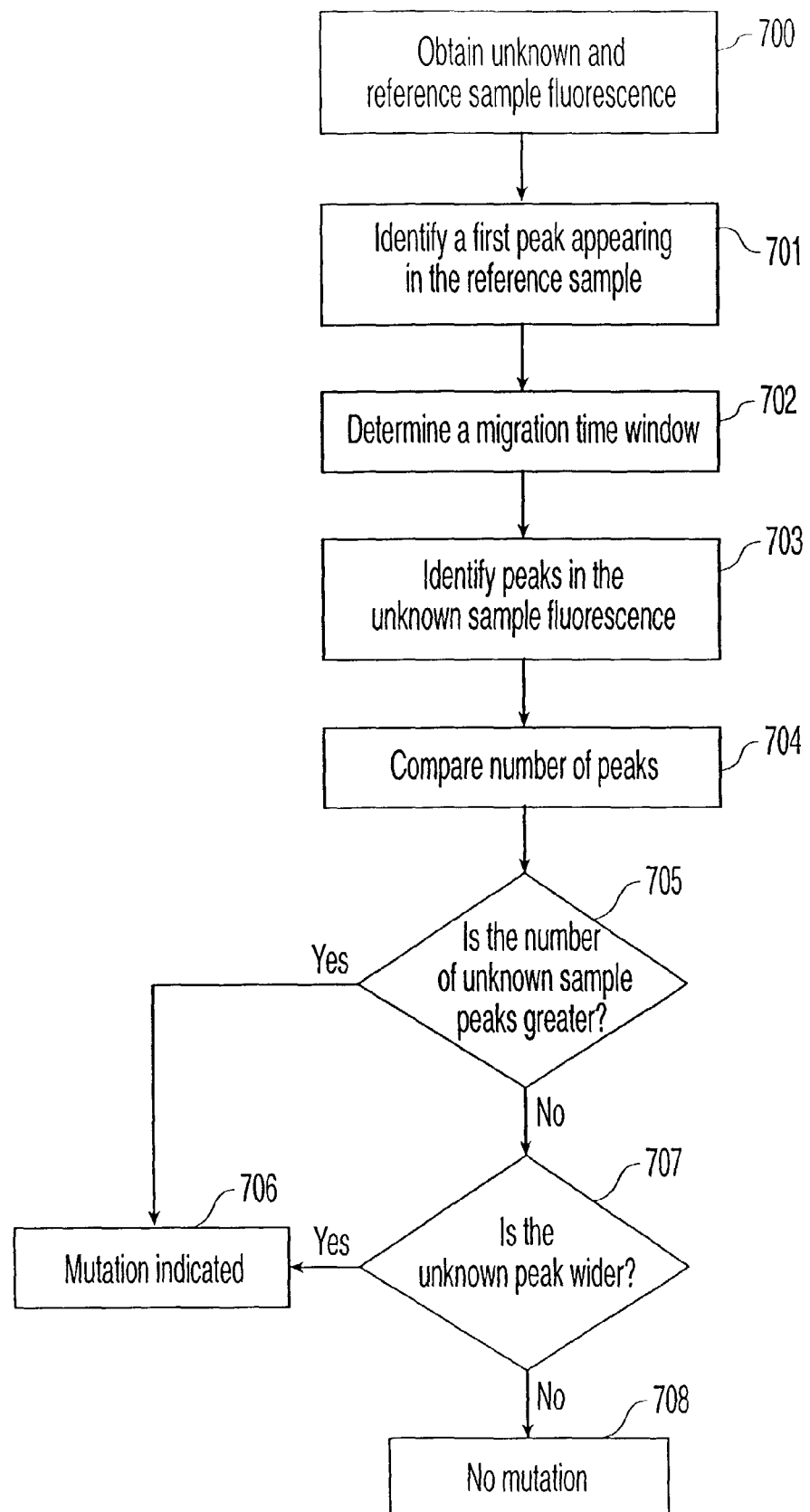
FIG. 6 shows a flow chart including steps for performing mutation detection.

Referring to a flow chart 609 shown in FIG. 6, one embodiment of mutation detection comprises comparing a first parameter representative of spectroscopic data resulting from an unknown sample with a second parameter representative of a spectroscopic data resulting from a reference sample. For example, the number of peaks appearing in the fluorescence data of an unknown sample can be compared with the number of peaks appearing in the fluorescence data of a reference sample. Flow chart 609 is followed when the reference sample comprises a homoduplex nucleotide. The mutation detection process begins by obtaining unknown and reference sample fluorescence 700. The mutation detection process further involves analysis of the fluorescence data, which analysis is preferably automated and performed by computer, which preferably includes software or a processor programmed to perform the detection process.

The automated comparison process includes identifying 701 a first peak in the reference sample. Peaks can be identified by, for example, establishing an intensity threshold that is greater than the average intensity in the electropherogram. Fluorescence data that have an intensity greater than the threshold intensity are identified as peaks.

A migration time window having a predetermined width is selected 702. The migration time window width is about 15%, preferably about 10% of the migration time of peak identified in the homoduplex fluorescence data. The migration time window is preferably centered about the peak in the homoduplex fluorescence data.

The number of peaks appearing within the migration time window of the fluorescence data of the unknown sample is determined 703 and compared 704 to the number of peaks in the migration time window of the reference sample fluorescence. Typically, there is only one peak in the reference sample migration time window. If the number of peaks in the migration time window of the unknown sample fluorescence exceeds the number of peaks in the migration time window of the reference sample, the presence of mutation is indicated 706.

If the number of peaks in the unknown sample fluorescence is not greater, the widths of the peaks are determined 707, as discussed above. If the width of the peaks in the unknown sample fluorescence exceeds the width of the corresponding peak in the reference sample fluorescence, the presence of mutation is indicated. If the widths of the peaks in the fluorescence of the unknown sample and the reference sample are the same 708, the absence of mutation is indicated.

When the number of peaks in the unknown sample fluorescence exceeds the number of peaks in the reference sample fluorescence, the presence of mutation is indicated with high confidence. A determination based upon peak width provides lesser assurance. However, a false positive is less of a concern than a false negative in clinical diagnosis, since further tests (such as sequencing) will be performed in these situations. The actual confidence level can be determined from the 2% RSD for the migration times and the level of the pattern change derived from curve fitting. Obviously, if one obtains a negative result in determining the presence of a mutation in an unknown sample, then the absence of a mutation in the unknown sample has been determined.

The method illustrated in flow chart 609 can be adapted for analyses performed using a reference sample that contains one or more mutations. Steps 700, 701, 702, 703, and 704 would be performed as described above. Steps 705, 706, 707, and 708 would be replaced by complementary steps that take account of the fact that, in this adapted method, the reference data would contain a plurality of peaks or a wide peak corresponding to the mutation.

While the above invention has been described with reference to certain preferred embodiments, it should be kept in mind that the scope of the present invention is not limited to these. Thus, one skilled in the art may find variations of these preferred embodiments which, nevertheless, fall within the spirit of the present invention, whose scope is defined by the claims set forth below.

What is claimed is:

1. A temperature gradient electrophoresis-based method for generating data indicative of the presence of a single nucleotide polymorphism or a mutation in a biological sample, comprising:
    providing an unknown double-stranded polynucleotide sample;
    subjecting the unknown double-stranded polynucleotide sample to temperature gradient gel electrophoresis, the unknown double-stranded polynucleotide sample including non-desalted polymerase chain reaction (PCR) products;
    subjecting a reference double-stranded polynucleotide to temperature gradient electrophoresis;
    irradiating the unknown double-stranded polynucleotide with light to generate a first spectroscopic signal, irradiating the reference double-stranded polynucleotide with light to generate a second spectroscopic signal;
    converting the first and second spectroscopic signals into first and second data; and
    determining the presence of a single nucleotide polymorphism or a mutation in the unknown double-stranded polynucleotide sample based on the first and second data.

2. The method of claim 1, wherein the spectroscopic signals are fluorescence signals.

3. The method of claim 1, wherein the spectroscopic signals are absorbance signals.

4. A method for determining the presence of a single nucleotide polymorphism or a mutation in a biological sample, comprising:
    determining a first parameter based on a first spectroscopic signal resulting from irradiating an unknown double-stranded polynucleotide sample with light the unknown double-stranded polynucleotide sample having been subjected to temperature gradient gel electrophoresis in the presence of non-desalted polymerase chain reaction (PCR) products;
    determining a second parameter based on a second spectroscopic signal resulting from irradiating a reference double-stranded polynucleotide sample with light, the reference double-stranded polynucleotide sample having been subjected to temperature gradient electrophoresis; and
    comparing the first and second parameters to determine whether there is a single nucleotide polymorphism or a mutation in the unknown double-stranded polynucleotide sample.

5. The method of claim 4, wherein the spectroscopic signals are fluorescence signals.

6. The method of claim 4, wherein the spectroscopic signals are absorbance signals.

7. A temperature gradient electrophoresis-based method for generating data indicative of the presence of a single nucleotide polymorphism or a mutation in a biological sample having single-stranded nucleic acid PCR products, comprising:
    providing an unknown double-stranded polynucleotide sample;
    subjecting the unknown double-stranded polynucleotide sample to temperature gradient electrophoresis in the presence of single-stranded DNA associated with PCR amplification of double-stranded polynucleotides of the unknown double-stranded polynucleotide sample;
    subjecting a reference double-stranded polynucleotide sample to temperature gradient electrophoresis;
    irradiating the unknown double-stranded polynucleotide sample with light to generate a first spectroscopic signal, and irradiating the reference double-stranded polynucleotide sample with light to generate a second spectroscopic signal;
    converting the first and second spectroscopic signals into first and second data; and
    determining the presence of a single nucleotide polymorphism or a mutation in the unknown double-stranded polynucleotide sample based on the first and second data.

8. A method for determining the presence of a single nucleotide polymorphism or a mutation in a biological sample having single-stranded nucleic acid PCR products, comprising:
    determining a first parameter based on a first spectroscopic time signal resulting from irradiating an unknown double-stranded polynucleotide sample with light, the unknown double-stranded polynucleotide sample having been subjected to temperature gradient electrophoresis in the presence of single-stranded DNA associated with PCR amplification of double-stranded polynucleotides of the unknown double-stranded polynucleotide sample;
    determining a second parameter based on a second spectroscopic time signal resulting from irradiating a reference double-stranded polynucleotide with light that has been subjected to temperature gradient electrophoresis; and
    comparing the first and second parameters to determine the presence of a single nucleotide polymorphism or a mutation in the unknown double-stranded polynucleotide.

9. A temperature gradient electrophoresis-based method for generating data indicative of the presence of a single nucleotide polymorphism or a mutation in a biological sample comprising first and second different unknown double-stranded polynucleotide samples, each of the samples comprising first and second member double-stranded polynucleotides, the members of the first sample and the members of the second sample being different sizes, comprising:
    while subjecting the first and second samples to electrophoresis within the same capillary in the presence of one another, changing the temperature at a first non-zero rate for a first period of time by an amount sufficient to change an electrophoretic mobility of the first member of the first unknown sample relative to an electrophoretic mobility of the second member of the first unknown sample and then changing the temperature at a second, different non-zero rate for a second period of time by an amount sufficient to change an electrophoretic mobility of the first member of the second unknown sample relative an electrophoretic mobility of the second member of the second unknown sample;
    irradiating the members of the first unknown sample with light to generate a first spectroscopic signal, and irradiating the members of the second unknown sample with light to generate a second spectroscopic signal; and determining the presence of a single nucleotide polymorphism or a mutation in the first unknown sample based on the first spectroscopic signal and determining the presence of a single nucleotide polymorphism or a mutation in the second unknown sample based on the second spectroscopic signal.

10. A method for determining the presence of a single nucleotide polymorphism or a mutation in a biological sample comprising first and second different unknown double-stranded polynucleotide samples, member double-stranded polynucleotides of the first unknown sample being a different size from member double-stranded polynucleotides of the second unknown sample, comprising:

determining a first parameter from a first spectroscopic signal obtained by irradiating the first unknown double-stranded polynucleotide sample with light;

determining a second parameter from a second spectroscopic signal obtained by irradiating the second unknown double-stranded polynucleotide sample with light wherein, prior to irradiating the first and second unknown polynucleotide samples with light, the first and second unknown polynucleotide samples were subjected to temperature gradient electrophoresis together along the sample capillary, wherein subjecting the first and second unknown double-stranded polynucleotide samples to electrophoresis comprised changing the temperature at a first non-zero rate for a first portion of the time and changing a temperature at a second, different and non-zero rate for a second portion of the time during the electrophoresis;

comparing each of the first and second parameters with a reference parameter to determine whether there is a single nucleotide polymorphism or a mutation in either of the first or second unknown double-stranded polynucleotide samples.

11. A capillary-based method for generating data indicative of the presence of a single nucleotide polymorphism or a mutation in a biological sample comprising first and second unknown double-stranded polynucleotides, member polynucleotides of the first unknown double-stranded polynucleotide sample being smaller than member polynucleotides of the second unknown double-stranded polynucleotide sample, the method comprising:

subjecting the first and second unknown double-stranded polynucleotide samples to electrophoresis together in the sample capillary;

during electrophoresis, changing the temperature of a central portion of the capillary from a first temperature $T_1$ to a second different temperature $T_2$;

irradiating the first unknown double-stranded polynucleotide sample with light to generate a first spectroscopic signal, and irradiating the second unknown double-stranded polynucleotide sample with light to generate a second spectroscopic signal;

converting the first and second pairs of spectroscopic signals into first and second data; and determining the presence of a single nucleotide polymorphism or mutation in the first unknown double-stranded polynucleotide sample based on the first data and determining the presence of a single nucleotide polymorphism or mutation in the second unknown double-stranded polynucleotide sample based on the second data.

12. In a method for detecting mutations in a polynucleotide sample by subjecting the polynucleotides to temperature gradient electrophoresis and obtaining spectroscopic intensity data indicative of the presence of the polynucleotides, the improvement comprising: thermally-contacting the sample polynucleotides with a chilled gas by contacting a capillary in which the polynucleotides are migrating with the chilled gas to reduce the temperature of the polynucleotides after the polynucleotides have been subjected to temperature gradient electrophoresis and prior to obtaining the spectroscopic intensity data.

13. The method according to claim 12, wherein the polynucleotides comprise homoduplex or heteroduplex DNA fragments.

14. The method of claim 12, wherein the temperature of the chilled gas has a temperature of less than about 15° C.

15. The method of claim 12, wherein actively reducing the temperature comprises thermoelectrically cooling the polynucleotides.

16. The method of claim 12, wherein actively reducing the temperature comprises thermally contacting the nucleotides with a chilled fluid.

17. The method according to claim 12, wherein, when the fluorescence intensity data are obtained, the temperature of the polynucleotides is less than about 30° C.

* * * * *